United States Patent [19]

Motz et al.

[11] 4,435,606
[45] Mar. 6, 1984

[54] PROCESS FOR THE PREPARATION OF LINEAR OLEFINS FROM TRIETHYLALUMINUM AND TRIPROPYLALUMINUM VIA GROWTH, ISOMERIZATION AND METATHESIS

[75] Inventors: Kaye L. Motz; Paul H. Washecheck; Ronald L. Poe; James E. Yates, all of Ponca City, Okla.

[73] Assignee: Conoco Inc., Ponca City, Okla.

[21] Appl. No.: 334,406

[22] Filed: Dec. 24, 1981

[51] Int. Cl.³ .......................... C07C 3/21; C07C 3/02
[52] U.S. Cl. ..................... 585/324; 585/314; 585/315; 585/316; 585/328; 585/329; 585/643; 585/645
[58] Field of Search ............... 585/315, 316, 324, 643, 585/645, 314, 328, 329

[56] References Cited

U.S. PATENT DOCUMENTS

| 3,358,050 | 12/1967 | Acciarri et al. | 585/324 |
| 3,647,906 | 3/1972 | Farley | 585/316 |
| 3,725,496 | 4/1973 | Kobylinski et al. | 585/645 |
| 3,776,974 | 12/1973 | Gautier et al. | 585/645 |
| 3,789,081 | 1/1974 | Lanier | 585/316 |
| 3,906,053 | 9/1975 | Lanier | 585/316 |
| 4,078,012 | 3/1978 | Blewett et al. | 585/645 |

OTHER PUBLICATIONS

Hawley, "The Condensed Chemical Dictionary", (Van Nostrand, p. 881.

Primary Examiner—Delbert E. Gantz
Assistant Examiner—A. Pal
Attorney, Agent, or Firm—Cortlan R. Schupbach, Jr.

[57] ABSTRACT

Internal olefins are subjected to metathesis closely coupled after an isomerization reaction to obtain desired molecular weight range linear olefins. Specific process steps and separation conditions are necessary to obtain the desired linear olefins.

27 Claims, 3 Drawing Figures

PROCESS FOR THE PREPARATION OF LINEAR OLEFINS FROM TRIETHYLALUMINUM AND TRIPROPYLALUMINUM VIA GROWTH, ISOMERIZATION AND METATHESIS

This invention relates to a process for altering the carbon atoms distribution of internal olefins to obtain olefin products controlled with respect to proportions. More particularly, this invention relates to such a process comprising passing a feed stream of internal olefins through a vessel containing an isomerization catalyst to randomize the double bond then immediately passing the randomized olefin product through a metathesis reactor to alter the carbon atoms distribution such that the average molecular weight of the product exiting this reactor is substantially equal to the feed olefin. At present, there are four commercial routes to linear olefins, two based on normal paraffin technology and two based on ethylene technology. The paraffin-based technologies are wax cracking to produce linear alpha-olefins and dehydrogenation of normal paraffins followed by separation of linear internal olefins. Both of these processes give generally poor quality olefins.

The ethylene-based routes are high temperature growth and displacement by ethylene of catalytic quantities of aluminum trialkyl to produce exponential distribution of linear alpha-olefins. Also an ethylene-based olefin process is used which produced on exponential distribution similar to that first described except for a reduction in the amount of 20 and higher carbon atom olefins. These processes produce predominantly lighter olefins having carbon atom contents ranging from about 4 to about 8.

A general description of art in this area can be found in *Chemical Technology*, Volume 8, 1979 by R. L. Banks. This article describes a metathesis reaction and gives general basic background of the reaction conditions and prior art of this reaction. U.S. Pat. No. 3,646,143 shows a metathesis catalyst in which silver or copper is added to metathesis catalyst to increase selectivity in methathesis of alpha olefins. U.S. Pat. No. 3,767,473 shows the metathesis of low molecular weight alpha olefins to produce higher molecular weight internal olefins together with the ozonolysis of internal olefins to produce low molecular weight carboxylic acids. U.S. Pat. No. 3,776,974 shows a process for taking alpha olefins from a growth process metathesizing with 2-butene to produce propylene and linear internal olefins. The internal olefins are then fractionated into lower and higher molecular weight fractions. This process significantly changes the molecular weight of the feed into that obtained by the product. U.S. Pat. No. 3,776,975 shows a metathesis of olefin mixtures containing at least 20% internal olefins, more than that predicted by an equilibrium mixture. The process is taught to extend catalyst life. U.S. Pat. No. 4,016,220 shows a metathesis reaction directed specifically to 9-tricosene and 9-heneicosene. However, the prior art, when taken in combination, changes the molecular weight between product and feed or else uses processes which are unduly cumbersome and expensive to operate. It would be greatly desirable to produce a process which allows the obtaining of a mixture of linear olefins from ethylene and propylene starting materials while maintaining a distribution of odd and even carbon number olefin homologues such that the mid-range homologues constitute a major portion of the entire mixture. In addition it would be desirable to provide a process wherein aluminum trialkyls used in the growth reaction can be recovered and recycled easily and inexpensively. In addition, the ability to maximize a certain carbon atom range of olefin would be highly desirable.

It is therefore an object of the present invention to provide a process for preparing a mixture of linear olefins from ethylene and propylene. Other objects will become apparent to those skilled in this art as the description proceeds.

It has now been discovered according to the present invention that a process for altering the carbon atom distribution of internal olefins to obtain olefin products controlled with respect to proportions is obtained by passing a feedstream of internal olefins through a vessel containing an isomerization catalyst to randomize the olefinic double bond, then passing the randomized olefin product through a metathesis reactor to alter the carbon atom distribution of linear olefin chains such that the distribution has an average molecular weight substantially equal to the feed olefins, then separating the product carbon atom range olefins from the product and recycling the unrecovered nonproduct carbon atom range internal olefins to either or both of the isomerization and/or metathesis reactor. Direct passage of the non-desired carbon atom olefins to the metathesis reactor is possible if done without exposure to oxygen such that re-purification of the stream is necessary.

The olefin feed to the process can be obtained from any source but is preferentially obtained from ethylene or ethylene and propylene using aluminum alkyl chemistry. The process comprises (a) reacting ethylene with aluminum trialkyl in the presence of an internal olefin solvent in a growth step to form aluminum alkyls and linear thermal alpha olefins;

(b) removing the inert internal olefin solvent and thermal linear alpha olefins formed containing up to about 14 carbon atoms as overhead in a fractional distillation;

(c) passing the remaining products of (b) into a vessel containing a transition metal catalyst and adding an alkene wherein aluminum alkyl and alpha olefins are formed in a displacement reaction;

(d) then passing the product of (c) through an isomerization reactor containing a transition metal catalyst to transform alpha olefins present into internal olefins, then (e) subjecting the product of (d) to separation to obtain internal olefins containing up to about 10 carbon atoms, a stream having olefins containing from about 10 to about 14 carbon atoms and aluminum trialkyls prepared by displacement in (c) and returning these 10 to 14 carbon atom materials to the growth reactor as solvent in recovered aluminum alkyl reactants while the overhead containing internal olefins up to about 10 carbon atoms together with thermal linear alpha olefins containing up to about 14 carbon atoms are recovered as product linear olefins. Once the product is obtained, the carbon atom distribution of the internal olefins to obtain desired olefin products controlled with respect to proportions is obtained comprising (1) passing a feedstream of said internal olefins through a vessel containing an isomerization catalyst to randomize the olefinic double bond;

(2) passing the randomized olefin product of (1) through a metathesis reactor to alter the carbon atoms distribution of linear olefin chains, wherein said distribution has an average molecular weight substantially equal to the feed olefins; then (3) separating the product carbon atom range olefins from the product, while (4) recycling the non-product carbon atom range internal olefins to 1, 2, or both 1 and 2.

Certain terminology used in the instant specification and claims is believed well understood in the art and is defined only for ready reference. "Trialkyl aluminum components" or "compounds" refers to aluminum compounds having three alkyl groups or alkyl group precursors which are the same or different. The term includes not only compounds such as triethyl aluminum or trihexyl aluminum, but other compounds such as diethyl aluminum hydride, dihexyl ethyl aluminum, aluminum trihydride and so forth. The hydride groups, if in high concentration, are rapidly and largely converted to alkyl groups in the presence of olefins at the operative conditions at various reactions in the process. Usually, a trialkyl aluminum stream has some small proportion of hydride groups.

"Chain growth" refers to the reaction of ethylene, propylene, 1-butene and mixtures of these with a trialkyl aluminum feed, wherein the alkyl groups are increased in average length by the addition of at least one (but usually more) moles of lower alkene per alkyl aluminum group, or per the carbon aluminum bonding of an alkyl aluminum moiety.

"Displacement" refers to the process, transfer or exchange of an alkyl group or an alkyl aluminum moiety by an alkyl corresponding to an olefin. The process is sometimes referred to as transalkylation. For example, the exchange of a hexyl group attached to aluminum and replacement by an ethyl group by reaction of a hexyl aluminum group with ethylene. "Alpha olefins" or "vinyl olefins" refer to straight chain olefins having a terminal ethylenic bond.

"Internal olefins" refers to non-alpha olefin compounds.

"Isomerization" refers to a process of moving a double bond from one position to another in the carbon chain. A specific example is moving the terminal bonding of a vinyl or alpha olefin to a position on the carbon chain such that the olefinic material is no longer an alpha olefin but rather an internal olefin.

In a preferred process, the product stream of (1) is close coupled to (2) such that air is excluded and the product stream cannot oxgenate. When this occurs, the stream need not be re-purified, but rather can be passed directly to the metathesis reactor, extending metathesis catalyst life nearly ten-fold. Such a process involves great savings in time, energy, and is much more efficient than those of the prior art.

In addition, additional linear olefin feed can be inserted into either 1 or 2 or both to allow close control of proportions.

In the isomerization reactor, the temperatures normally range from about 25° C. to about 200° C. and pressures of from about atmospheric to about 200 pounds per square inch gauge (psig) are used. Normally the isomerization is carried out in the presence of a catalyst comprising sodium on an alumina support.

The metathesis reaction is normally carried out at temperatures of from about 50° C. to about 200° C. and pressures from about atmospheric to about 200 pounds per square inch gauge. The metathesis reaction is usually carried out in the presence of a catalyst comprising molybdenum on an alumina support. Cobalt can optionally be added to the molybdenum.

In the metathesis reaction, normally the mole ratio of cobalt to molybdenum is from about 0:1 to about 1:3 and the ratio of both cobalt and molybdenum to the alumina support is from about 1:100 to about 1:3 respectively. Cobalt, however, is not necessary in this catalyst.

Although any convenient separation technique can be used, fractional distillation is preferred because of its inexpensive operation and ease of control. As will be well recognized by those skilled in the art, fractional distillation can be adjusted to obtain virtually any carbon atom cut with only a slight degree of overlap. Certain fractions recovered can be recycled to various points in the process to provide an efficient operation. Normally the isomerization reactor, as well as containing the original feed, will contain recycled fractions containing from about 3 to about 10 and from about 15 to about 30 internal alkene. However, if oxygen is excluded from these streams, the fractions containing from about $C_3$ to about $C_{10}$ and from about $C_{15}$ to about $C_{30}$ internal alkenes can be recycled directly to the metathesis reactor. Of course it will be realized to those skilled in the art that any number of fractions containing anywhere from about $C_3$ to about $C_{30}$ alkenes can be recovered as product.

The invention is more concretely described with reference to the examples and figures below wherein all parts and percentages are by weight unless otherwise specified. The examples are provided to illustrate the present invention and not to limit it.

In the figures,

FIG. 3 is a schematic showing in more detail the relationship between the separation steps and the isomerization and metathesis of the present invention. In FIG. 3 the optional recycle is likewise shown.

A more specific description of the instant invention is set forth below.

Figure 1:
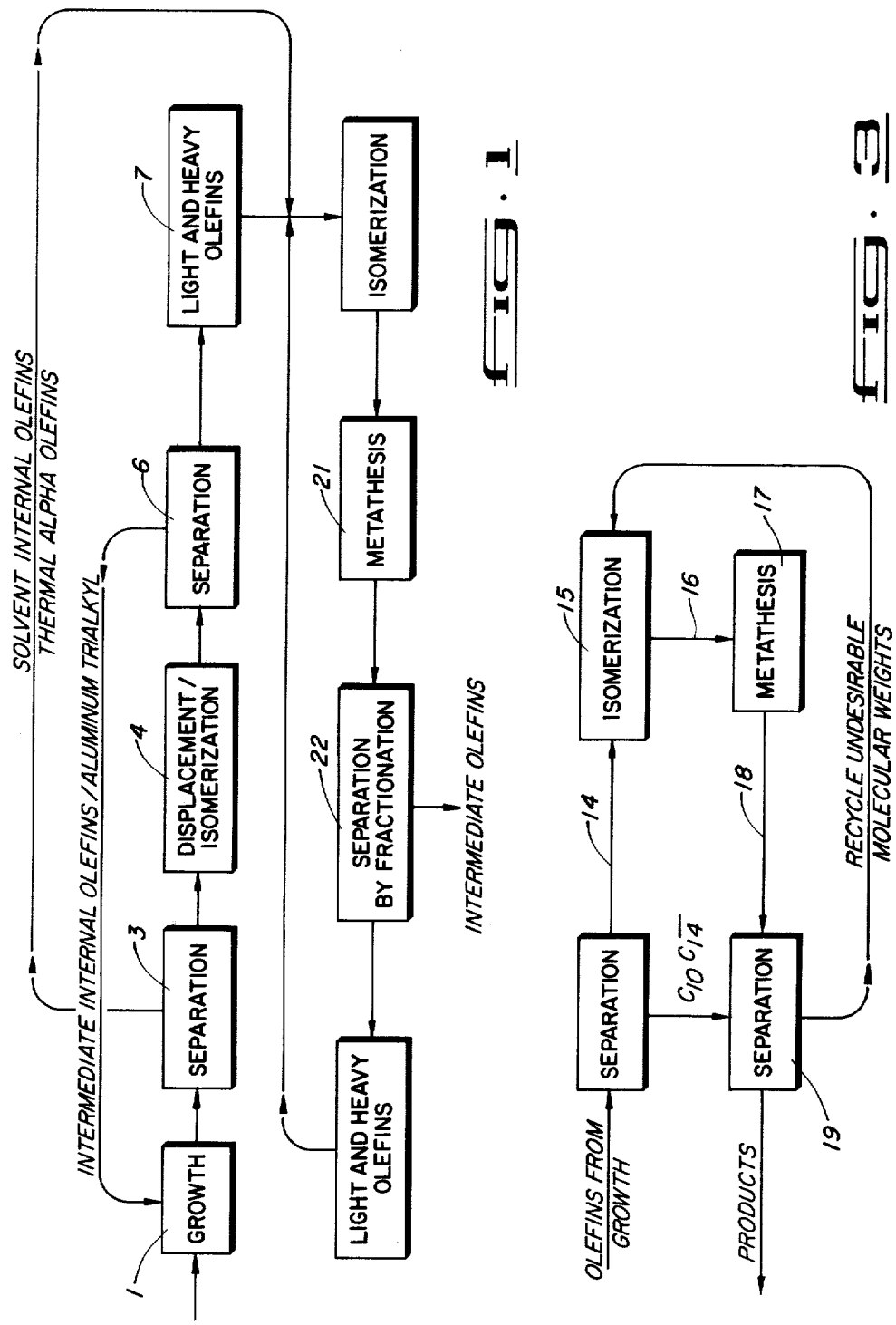
FIG. 1 shows a generalized schematic of the preferred process for obtaining olefins using the present invention.

FIG. 1 illustrates a growth step (1) wherein ethylene reacts with aluminum triethyl or a mixture of aluminum triethyl and aluminum tripropyl to form both even and odd carbon number long chain aluminum alkyl (growth product) and a smaller amount of linear olefins.

In the separation step (3) immediately following the growth reaction, solvent and olefins up to about 14 carbon atoms are stripped from the growth product by flash distillation. In the displacement/isomerization step (4), ethylene and propylene react with the stripped growth product in separate parallel reactors (see FIG. 2) to form mixtures of linear internal olefins and aluminum triethyl (ATE) in the case of ethylene displacement and aluminum tripropyl (ATP) in the case of propylene displacement. Both displacement/isomerization reactions are catalyzed by a transition metal. Normally, nickel is the preferred catalyst for such reactions. Of course, those skilled in the art will realize that if aluminum tripropyl is not used, FIG. 2 would require only 1 displacement/isomerization reactor and flash unit in order to be effective.

In the second separation (6) following displacement/isomerization sequential distillations are used to produce an overhead fraction containing up to about 11 carbon atom olefins, an overhead fraction containing from about $C_{12}$ to about $C_{14}$ olefins together with aluminum triethyl and aluminum tripropyl and a bottoms fraction containing from 15 and higher olefins.

The fraction containing $C_{12}$ and $C_{14}$ internal olefins, ATE and ATP (ATA, aluminum trialkyls), is returned to the growth step (20). The $C_{12}$ to $C_{14}$ internal olefins serve as a growth solvent which is recovered in the first separation following the growth step. The olefin fractions are sent to a cleanup step where any small amounts of aluminum alkyls and catalysts which may be present are removed.

The process of the present invention produces an olefin mixture containing both even and odd carbon number homologues in separate poisson distributions which are determined by the relative quantities of the ATE and ATP charge to the growth reaction and the average number of ethylene molecules added per aluminum-carbon bond. In the metathesis step, the isomerized olefins are passed through a bed of cobalt and molybdenum on alumina to produce a new distribution of linear carbon chains having the same average molecular weight as the feed olefins.

In the third separation (22) following the metathesis (21) step, internal olefins are separated by distillation into desired fractions. Normally, such fractions would contain from 3 to 5 carbon atoms, from 6 to 10 carbon atoms, from 11 to 12 carbon atoms, from 13 to 14 carbon atoms, and from 15 to 30 carbon atoms, together with a bottoms fraction.

Figure 2:
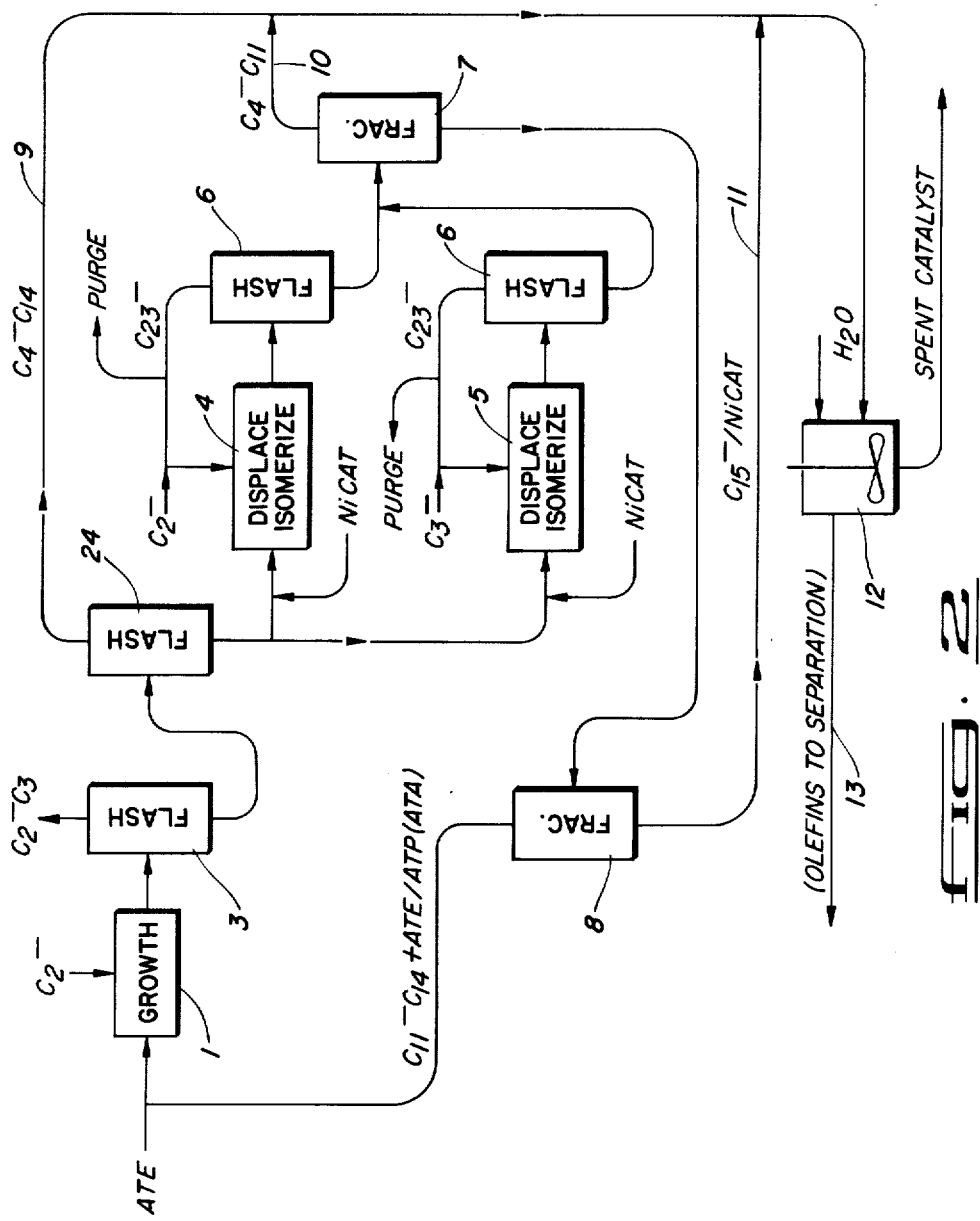
FIG. 2 shows a more detailed schematic of the process of the present invention wherein the various feeds, recycles and displacement/isomerizations can be seen.

FIG. 2 illustrates the process schematically, wherein linear olefins are produced from ethylene and propylene. In the process, ethylene reacts with ATE and ATP in a growth reactor (1) to form long chain aluminum alkyls. The growth product is then treated to remove excess ethylene (3) and any other olefins present up to about 14 carbon atoms. The growth product is then reacted with more ethylene in a displacement/isomerization reactor (4) and, if propylene is present, with propylene in a separate parallel displacement/isomerization reactor (5). Both reactions occur in the presence of a catalyst to produce mixtures of long chain internal olefins and ATE in the ethylene reactor (ATP in the propylene reactor). The displacement and isomerization reactions are normally carried out in staged reactors where conditions are adjusted so as to favor displacement in the first stage and isomerization in the second stage. The conditions are also optimized for the particular displacement system involved (whether ethylene or propylene is involved). Alternatively, a batch system can be used, where the reactor is charged under conditions favoring displacement, followed by pressure reduction to provide conditions suitable for isomerization. However, the continuous staged reactor, where pressure is reduced in an isomerization stage, is preferred.

The displacement/isomerization products are sent to flash drums (6) where excess ethylene and propylene are removed. From the flash drums the product goes to a distillation tower (7) to remove olefins up through about 11 carbon atoms, and then to a second tower (8) which takes overhead a fraction containing from about $C_{12}$ to $C_{14}$ internal olefins, ATE and ATP. This recovered overhead fraction is recycled to the growth reactor (1) to produce more growth product. The $C_{12}$ to $C_{14}$ internal olefins in this stream are recovered as part of the overhead fraction (9) from the growth product stripping section immediately following the growth reactor. These olefins, plus those taken overhead in the displacement product fractionation (10), together with the heavier olefins from the bottoms (11), can be combined and sent to a clean-up step (12) in which catalyst and any residual aluminum alkyls are recovered. The crude olefin is then sent to fractionation (13) for separation into the carbon atom ranges desired.

The intermediate olefins containing from about 10 to 14 carbon atoms are taken as products while the light and heavy olefins are sent to isomerization and metathesis for redistribution. It should be noted that a second pass through the isomerization bed for these products is not necessary if oxygen is excluded from the products. In this case the olefins may be sent directly to metathesis for redistribution. The redistributed olefins are separated again with the intermediates being taken as products and light and heavy olefins again recycled to isomerization and metathesis.

Those skilled in the art will realize that olefins not derived from the process can be incorporated into the process at any time up to this point. Thus, butene or propylene could be added to the metathesis section as desired, should average molecular weight considerations make such additions desirable.

Another option of the instant invention allows the amount of intermediate olefin produced upon metathesis to be increased by bypassing isomerization with a light olefin. This would increase the number of 5, 6, 7 and 8 fragments in the mixture, which would lead to the production of more intermediate olefins.

FIG. 3 shows a schematic of the separation, isomerization and metathesis steps. Olefins are sent to an isomerization step through which any alpha olefins present are transformed into internal olefins. An isomerization reactor uses a catalyst which randomizes the double bond placement such that only about 2% alpha olefins remain. The olefins can be either even or odd homologues of the starting material, depending on whether aluminum triethyl, aluminum tripropyl or both are used to feed the isomerization reactor.

Product stream exiting the isomerization reactor (15) through line 16 goes directly into a metathesis reactor (17). The metathesis reactor is normally close coupled to the isomerization reactor so as to provide a very short transit time and exclude oxygen from the product stream. This reaction is carried out at pressures and temperatures as previously described, i.e. 50° C. to about 200° C. and pressures of from about atmospheric to about 200 psig in the presence of a catalyst comprising molybdenum on an alumina support. Cobalt can optionally be used in addition to molybdenum.

Olefins in the desired carbon atom range, in this instance about 10 to about 14 carbon atoms may be taken as products or may be combined with light and heavy olefins and sent to isomerization and metathesis for redistribution. The redistributed olefins are separated again with the intermediates being taken as products and the light and heavy olefins again recycled to isomerization and metathesis. In the process this is shown in FIG. 3 as exiting the metathesis reactor (17) through line 18 to a second reactor separation (19), wherein about 10 to 14 carbon atom olefins are taken as products while the light and heavy olefins are sent to isomerization and metathesis for redistribution. The olefins which are redistributed are separated again with the intermediates being taken as products and the light and heavy olefins again recycled to isomerization and metathesis.

Many of the products which are in excess of demand at any given time can, of course, be recycled to the isomerization metathesis reactor for redistribution and recovery of more desirable carbon atom weights.

Thus the present invention prepares a mixture of linear olefins from ethylene or ethylene and propylene. The mixture contains a distribution of olefin homologues such that the mid range homologues such as $C_{10}$ to $C_{14}$ constitute a major portion of the entire mixture. The present invention likewise produces linear olefins in a process in which the aluminum trialkyls used in a growth reaction can be recovered and recycled by relatively simple distillation process. The instant invention allows selection of olefins having a desired carbon atom range to meet shifting demand by simply recycling undesired olefin carbon atom ranges back through the process and recovering only the desired cuts.

The instant invention is more concretely described with reference to the examples below wherein all parts and percentages are by weight unless otherwise specified. The examples are provided to illustrate the present invention and not to limit it.

EXAMPLE 1

With reference to FIG. 2, about 250 parts per hour of a mixture containing about 100 parts aluminum triethyl (ATE) and about 150 parts $C_{10}$–$C_{14}$ internal olefins are fed to the growth reactor (1) along with about 575 parts per hour of ethylene. This reactor operates from about 1000 to 2000 pounds per square inch gauge (psig) pressure and about 100° C. to 130° C. temperature. The growth reactor effluent is sent through a flash distillation system (3) which removes approximately 40 parts ethylene and about 200 parts of $C_4$–$C_{14}$ olefins of which about 150 parts are internal $C_{10}$–$C_{14}$ olefins. The $C_4$–$C_{14}$ olefin fraction is taken as a portion of the olefin product. About 585 parts per hour of bottoms product from the flash unit are charged to the displacement-/reactor (4) along with approximately 170 parts per hour of ethylene and 0.08 parts per hour of nickel octanoate (6% Ni). This reactor is a batch-type reactor, which for displacement reactions operates at around 90°–95° C. and around 800–1000 psig pressure, with a product residence time of about 0.5–1 hour. The displaced product from this reactor passes through a flash drum where the ethylene pressure is reduced to approximately 50 psig and from the flash drum back into the reactor where the product displaced is maintained at isomerization conditions at around 90°–95° C. for about 3 to 5 hours. The effluent from the isomerization reactor is passed through a flash drum (6) where excess ethylene is removed and then into a distillation train. The light olefin tower removes an overhead fraction of about 100 parts per hour of $C_4$–$C_{10}$ internal olefin (10). Following this, the ATE tower (8) produces about 250 parts per hour of an overhead cut that is approximately 40% ATE and approximately 60% $C_{10}$–$C_{14}$ internal olefin. This fraction is recycled to the growth reactor along with any make up ATE necessary to maintain the proper amount of aluminum in the growth reactor. The bottoms from the ATE tower are sent to the heavy olefins tower (12) where about 200 parts per hour of $C_{14}$–$C_{30}$ internal olefins are produced as an overhead product (13). This olefin along with that from the light olefin tower (7) and from the growth product flash unit (24) make up the total olefin product from the process. These olefins consist of linear even carbon number homologs and are a mixture of internal isomers of which the 2-isomer is predominant.

Upon attainment of steady state operation the olefins produced would have a composition as described below if an "m" value of 5.0 were obtained in the growth reaction.

| | | | |
|---|---|---|---|
| $C_2$ | 0.69% | $C_{20}$ | 5.49% |
| $C_4$ | 3.38% | $C_{22}$ | 3.05% |
| $C_6$ | 6.95% | $C_{24}$ | 1.53% |
| $C_8$ | 10.67% | $C_{26}$ | 0.70% |
| $C_{10}$ | 14.29% | $C_{28}$ | 0.29% |
| $C_{12}$ | 16.14% | $C_{30}$ | 0.11% |
| $C_{14}$ | 15.37% | $C_{32}$ | 0.04% |
| $C_{16}$ | 12.51% | $C_{34}$ | 0.01% |
| $C_{18}$ | 8.83% | | |

A mixture of 100 parts of the above olefin mixture and 476 parts of recycle olefins from which the $C_{11}$ to $C_{14}$ olefins have been removed are sent to the isomerization reactor. The isomerization reactor is a packed bed of 7.5% sodium deposited on CATAPAL SB alumina (trademark of and sold by Conoco Inc.) operated at 50° C. at 200 psig with a weight hourly space velocity of 1. The isomerized olefins are allowed to flow directly to a metathesis reactor which is a bed of cobalt molybdenum hydrodesulfurization catalyst which has been activated at 550° C. The metathesis reactor is operated at 125° C., 200 psig with a weight hourly space velocity of 1.

The products of the metathesis reactor are distilled into three overhead fractions. Fraction one contains olefins with up to eleven carbon atoms; fraction two, those with 11 to 14 carbon atoms; and fraction three, those with 15 carbon atoms and above. A bottoms fraction containing olefins with more than 30 carbon atoms is discarded.

Fraction one and three are returned either to the isomerization reactor or the metathesis reactor as appropriate to the products desired while fraction two is taken as the product fraction.

Based on a fresh feed rate of 100 parts, 98 parts of $C_{11}$ to $C_{14}$ olefins are obtained as products with a distribution of 32% $C_{11}$, 26% $C_{12}$, 22% $C_{13}$ and 20% $C_{14}$.

EXAMPLES 2 THROUGH 8

The effect of directly passing isomerized olefin into a metathesis reactor was measured. The equilibrium product of a single pass of 1-dodecene through an isomerization reactor was fed into metathesis reactor containing a bed of cobalt molybdenum catalyst. Reaction conditions in the metathesis reactor were 125° C., 200 psig and a weight hourly space velocity (WHSV) of 1.0. The equilibrium product was passed through a silica gel bed to remove metathesis catalyst deactivating peroxides in examples 2 through 7. In example 8, the isomerized product was fed directly into the metathesis reactor without collection, storage, or treatment. The effect on catalyst life is set forth in Table 1.

TABLE 1

METATHESIS CATALYST LIFE AS A
FUNCTION OF STORAGE TIME
BETWEEN ISOMERIZATION OVER $Na/Al_2O_3$
And metathesis over $CoMo/Al_2O_3$

| Example | Storage Time-Days | Percolation Treatment | Metathesis Catalyst Life/Hrs | Comments |
|---|---|---|---|---|
| 2 | ca 60 | Silica gel | 127 | First time container opened |

TABLE 1-continued
METATHESIS CATALYST LIFE AS A
FUNCTION OF STORAGE TIME
BETWEEN ISOMERIZATION OVER Na/Al$_2$O$_3$
And metathesis over CoMo/Al$_2$O$_3$

| Example | Storage Time-Days | Percolation Treatment | Metathesis Catalyst Life/Hrs | Comments |
|---|---|---|---|---|
| | | | | since storage |
| 3 | 66 | Silica gel | 95 | |
| 4 | 74 | Silica gel | 76 | |
| 5 | 89 | Silica gel | 46 | |
| 6 | 96 | Silica gel | 22 | |
| 7 | 0 | Silica gel | 142 | Freshly isomerized |
| 8 | — | Silica gel | ca 1000 | Isomerized olefin fed directly from reactor into metathesis reaction |

While certain embodiments and details have been shown for the purpose of illustrating this invention, it will be apparent to those skilled in this art that various changes and modifications may be made herein without departing from the spirit or scope of the invention.

We claim:

1. A process for extending catalyst life during the alteration of the carbon atom distribution of internal olefins to obtain internal olefin products containing a majority of mid-range homologues wherein air or oxygen is excluded from the olefins throughout the process from growth through metathesis, the process comprising (1) reacting ethylene with aluminum trialkyl in the presence of an internal olefin solvent in a growth step to form aluminum alkyls and linear thermal alpha olefins;

(2) removing the inert internal olefin solvent comprising from 10 to 14 carbon atoms and thermal linear alpha olefins formed containing up to about 14 carbon atoms as overhead in a fractional distillation, and passing these olefins to isomerization in step 5(a);

(3) passing the remaining products of (2) into a vessel containing a transition metal catalyst and adding ethylene or ethylene and propylene wherein aluminum alkyl and alpha olefins are formed in a displacement reaction;

(4) passing the product of (3) through an isomerization reactor containing a transition metal catalyst to transform alpha olefins present into internal olefins, then (5) subjecting the product of (4) to separation to obtain internal olefins containing up to about 10 carbon atoms, a stream containing from 15 to 30 carbon atom internal olefins and a stream having internal olefins containing from about 10 to about 14 carbon atoms and aluminum trialkyls prepared by displacement in (3) and returning these 10 to 14 carbon atom materials to the growth reactor as solvent and recovered aluminum alkyl as a reactant, while the overhead containing internal olefins up to about 10 carbon atoms together with the overhead stream from step 2 are combined and wherein the carbon atom distribution of both the alpha-olefins and internal olefins is altered to obtain internal olefins controlled with respect to proportions by (a) passing a feedstream of internal olefins containing up to about 10 carbon atoms and from about 15-30 carbon atoms together with the mixture of 10-14 carbon atom internal olefins and up to 14 carbon atom alpha-olefins from the separator following growth through a vessel containing an isomerization catalyst to randomize the internal olefinic double bond, and (b) passing the randomized internal olefin product of (a) through a closely coupled metathesis reactor to alter the carbon atom distribution of linear carbon chains, said distribution having an average molecular weight substantially equal to the feed internal olefins, then (c) separating product carbon atom range internal olefins from the product, while (d) recycling non-product carbon atom range internal olefins to (a), (b), or both.

2. A process as described in claim 1 wherein additional C$_3$ or C$_4$ alkene feed is inserted into (5a), (5b), or both.

3. A process as described in claim 2 wherein the isomerization is carried out at a temperature of from about 25° C. to about 200° C. and a pressure of from about atmospheric to about 2000 psig.

4. A process as described in claim 3 wherein the isomerization is carried out in the presence of a catalyst comprising sodium on an alumina support.

5. A process as described in claim 4 wherein the metathesis is carried out at a temperature of from about 50° C. to about 200° C. and a pressure of from about atmospheric to about 2000 psig.

6. A process as described in claim 5 wherein the metathesis is carried out in the presence of a catalyst comprising molybdenum on an alumina support.

7. A process as described in claim 6 wherein cobalt is used in addition and wherein the mole ratio of Co to Mo is from about 0:1 to about 1:3 and wherein the ratio of both Co and Mo to the alumina support is from about 1:100 to about 1:3.

8. A process as described in claim 7 wherein the product stream of (1) contains only even number carbon homologs.

9. A process as described in claim 8 wherein the separation of (5c) is carried out using fractional distillation.

10. A process as described in claim 9 wherein successive fractionations are carried out.

11. A process as described in claim 9 wherein ethylene is fractionated as an overhead and recovered.

12. A process as described in claim 11 wherein fractions are recovered as overhead and are recycled as feed to (1).

13. A process as described in claim 10 wherein fractions are recovered as overhead and recycled to (5a).

14. A process as described in claim 12 wherein any number of fractions containing C$_3$ to C$_{10}$ and C$_{15}$ to C$_{30}$ internal alkenes are recycled to (5a).

15. A process as described in claim 12 wherein any number of fractions containing C$_3$ to C$_{10}$ and C$_{15}$ to C$_{30}$ internal alkenes are recycled to (5a).

16. A process as described in claim 12 wherein any number of fractions containing C$_3$ to C$_{30}$ alkenes are recovered as product.

17. A process as described in claim 12 wherein C$_{31}$+ alkenes are disposed.

18. A process as described in claim 7 wherein the product stream of (1) contains both even and odd number carbon homologs.

19. A process as described in claim 18 wherein the separation of (5c) is carried out using fractional distillation.

20. A process as described in claim 19 wherein successive fractionalizations are carried out.

21. A process as described in claim 20 wherein ethylene is separated as an overhead and recovered.

22. A process as described in claim 21 wherein fractions are recovered as overhead and are recycled as feed to (1).

23. A process as described in claim 20 wherein fractions are recovered as overhead and recycled to (5a).

24. A process as described in claim 22 wherein any number of fractions containing $C_3$ to $C_{10}$ and $C_{15}$ to $C_{30}$ internal alkenes are recycled to (5a).

25. A process as described in claim 22 wherein any number of fractions containing $C_3$ to $C_{10}$ and $C_{15}$ to $C_{30}$ internal alkenes are recycled to (5a).

26. A process as described in claim 22 wherein any number of fractions containing $C_3$ to $C_{30}$ alkenes are recovered as product.

27. A process as described in claim 22 wherein $C_{31}+$ alkenes are disposed.

* * * * *